(12) United States Patent
Winslow et al.

(10) Patent No.: US 9,138,463 B2
(45) Date of Patent: *Sep. 22, 2015

(54) MALPEG-HB CONJUGATE-CONTAINING COMPOSITIONS FOR DELIVERING CARBON MONOXIDE (CO) TO CELLS

(76) Inventors: Robert M. Winslow, La Jolla, CA (US); Nancy Jo Winslow, legal representative, La Jolla, CA (US); Kim Vandegriff, San Diego, CA (US); Ashok Malavalli, San Diego, CA (US)

(*) Notice: Subject to any disclaimer, the term of this patent is extended or adjusted under 35 U.S.C. 154(b) by 993 days.

This patent is subject to a terminal disclaimer.

(21) Appl. No.: 13/276,992

(22) Filed: Oct. 19, 2011

(65) Prior Publication Data

US 2012/0094912 A1    Apr. 19, 2012

Related U.S. Application Data

(63) Continuation of application No. 12/233,467, filed on Sep. 18, 2008, now abandoned, which is a continuation of application No. 11/370,502, filed on Mar. 7, 2006, now abandoned.

(60) Provisional application No. 60/659,137, filed on Mar. 7, 2005.

(51) Int. Cl.
*A61K 38/42* (2006.01)
*A61K 33/00* (2006.01)
*A61K 47/48* (2006.01)

(52) U.S. Cl.
CPC ............ *A61K 38/42* (2013.01); *A61K 33/00* (2013.01); *A61K 47/48215* (2013.01); *A61K 47/48307* (2013.01)

(58) Field of Classification Search
None
See application file for complete search history.

(56) References Cited

U.S. PATENT DOCUMENTS

| | | | |
|---|---|---|---|
| 6,087,087 A | 7/2000 | Yonetani et al. | |
| 6,627,738 B2 | 9/2003 | Stamler et al. | |
| 6,844,317 B2 | 1/2005 | Winslow et al. | |
| 2002/0037839 A1 | 3/2002 | Stamler et al. | |
| 2003/0039638 A1 | 2/2003 | Bach et al. | |
| 2003/0064114 A1 | 4/2003 | Motterlini et al. | |
| 2003/0149307 A1 | 8/2003 | Hai et al. | |
| 2003/0153491 A1 | 8/2003 | Winslow et al. | |
| 2003/0162693 A1 | 8/2003 | Winslow et al. | |
| 2012/0094936 A1* | 4/2012 | Winslow et al. | 514/21.2 |

FOREIGN PATENT DOCUMENTS

| | | | |
|---|---|---|---|
| WO | 91/07190 A1 | 5/1991 | |
| WO | 94/22482 A1 | 10/1994 | |
| WO | 96/30006 A1 | 10/1996 | |
| WO | 96/34889 A1 | 11/1996 | |
| WO | 03/059363 A1 | 7/2003 | |
| WO | 2004/054433 A2 | 7/2004 | |
| WO | 2004/058291 A1 | 7/2004 | |

OTHER PUBLICATIONS

Amberson, W. R., "Clinical Experience with Hemoglobin-Saline Solutions," Science, Aug. 1947, p. 117, vol. 106, No. 2745.
Beutler, E., "The Effect of Carbon Monoxide on Red Cell Life Span in Sickle Cell Disease," Blood, Aug. 1975, pp. 253-259, vol. 46, No. 2.
Blumenstein, J., et al., "Experimental Transfusion of Dextran-Hemoglobin," Progress in Clinical and Biological Research, 1978, pp. 205-212, vol. 19.
Brouard, S., et al., "Carbon Monoxide Generated by Heme Oxygenase 1 Suppresses Endothelial Cell Apoptosis," The Journal of Experimental Medicine, Oct. 2000, pp. 1015-1026, vol. 192, No. 7.
Doherty, D. H., et al., "Rate of Reaction with Nitric Oxide Determines the Hypertensive Effect of Cell-Free Hemoglobin," Nature Biotechnology, Jul. 1998, pp. 672-676, vol. 16, No. 7.
Gonzales, R. J., et al., "Role of CO in Attenuated Vasoconstrictor Reactivity of Mesenteric Resistance Arteries After Chronic Hyopxia," American Journal of Physiology. Heart and Circulatory Physiology, 2002, pp. H30-H37, vol. 282, No. 1.
Guo Y., et al., "Administration of a CO-Releasing Molecule at the Time of Reperfusion Reduces Infarct Size in Vivo," American Journal of Physiology. Heart and Circulatory Physiology, 2004, pp. H1649-H1653, vol. 286, No. 5.
Hess, J., et al., "Pulmonary and Systemic Hypertension After Hemoglobin Administration," Blood, Abstract, 1991, p. 356A, vol. 78.
Juszczak, L. J., et al., "UV Resonance Raman Study of beta93-Modified Hemoglobin A: Chemical Modifier-Specific Effects and Added Influences of Attached Poly(ethylene glycol) Chains," Biochemistry, 2002, pp. 376-385, vol. 41, No. 1.
Keipert, P. E., et al., "Acute Changes in Systemic Blood Pressure and Urine Output of Conscious Rats Following Exchange Transfusion with Diaspirin-Crosslinked Hemoglobin Solution," Transfusion, Sep. 1993, pp. 701-708, vol. 33, No. 9.
Lemon, D. D., et al., "Control of the Nitric Oxide-Scavenging Activity of Hemoglobin," Art. Cells, Blood Subs., and Immob. Biotech., 1996, p. 378, vol. 24.
Liebhaber, S. A., et al., "Cloning and Complete Nucleotide Sequence of Human 5'-alpha-globin Gene," Proceedings of the National Academy of Sciences of the United States of America, Dec. 1980, pp. 7054-7058, vol. 77, No. 12.
Lin, Y., et al., "Long-Term Survival of Hamster Hearts in Presensitized Rats," Journal of Immunology, May 2000, pp. 4883-4892, vol. 164, No. 9.
Marotta, C. A., et al., "Human beta-Globin Messenger RNA. III. Nucleotide Sequences Derived From Complementary DNA," The Journal of Biological Chemistry, Jul. 1977, pp. 5040-5053, vol. 252, No. 14.
Nagai, K, et al., "Oxygen Binding Properties of Human Mutant Hemoglobins Synthesized in *Escherichia coli*," Proceedings of the National Academy of Sciences of the United States of America, Nov. 1985, pp. 7252-7255, vol. 82, No. 21.
Otterbein, L. E., et al., "Carbon Monoxide Suppresses Arteriosclerotic Lesions Associated with Chronic Graft Rejection and with Balloon Injury," Nature Medicine, 2003, pp. 183-190, vol. 9, No. 2.

(Continued)

*Primary Examiner* — Anand Desai
(74) *Attorney, Agent, or Firm* — Senniger Powers LLP

(57) ABSTRACT

The present invention relates to compositions for delivering carbon monoxide (CO) to cells using heme proteins as carriers. In one embodiment, the present invention relates to the use of MalPEG surface modified hemoglobin to deliver CO to cells.

20 Claims, 17 Drawing Sheets

(56) References Cited

OTHER PUBLICATIONS

Rohlfs, R. J., et al., "Arterial Blood Pressure Responses to Cell-Freee Hemoglobin Solutions and the Reaction with Nitric Oxide," The Journal of Biological Chemistry, May 1998, pp. 12128-12134, vol. 273, No. 20.

Roughton, F. J., et al., "The Fate of CO in the Body During Recovery from Mild Carbon Monoxide Poisoning in Man," The American Journal of Physiology, Dec. 1945, pp. 239-252, vol. 145.

Severinghaus, et al., "Oxygen Dissociation Curve Analysis at 98.7%-99.6% Saturation" in "Oxygen Affinity of Hemoglobin and Red Cell Acid Base Status," 1972, pp. 67-72, Astrup and Rorth, Eds., Academic Press, New York, New York.

Thiemermann, C., "Inhaled CO: Deadly Gas or Novel Therapeutic?," Nature Medicine, May 2001, pp. 534-535, vol. 7, No. 5.

Vandegriff, K. D., et al., "Kinetics of NO And O2 Binding to a Maleimide Poly(ethylene glycol)-Conjugated Human Haemoglobin," The Biochemical Journal, Aug. 2004, pp. 183-189, vol. 382, Part 1.

Winslow, R. M., "AlphaAlpha-Crosslinked Hemoglobin: Was Failure Predicted by Preclinical Testing?," Vox Sanguinis, 2000, pp. 1-20, vol. 79, No. 1.

Zhang, F., et al., "Vasoregulatory Function of the Heme-Heme Oxygenase-Carbon Monoxide System," American Journal of Hypertension, Jun. 2001, pp. 62S-67S, vol. 14, No. 6, Part 2.

* cited by examiner

MALPEG-HB CONJUGATE-CONTAINING COMPOSITIONS FOR DELIVERING CARBON MONOXIDE (CO) TO CELLS

RELATED APPLICATIONS

This application is a continuation application of U.S. Utility application Ser. No. 12/233,467, which was filed on Sep. 18, 2008, which is a continuation of U.S. Utility application Ser. No. 11/370,502, which was filed on Mar. 7, 2006, which claims the benefit of U.S. Provisional Application Ser. No. 60/659,137, which was filed on Mar. 7, 2005, each of which are incorporated herein by reference.

FIELD OF THE INVENTION

The present invention relates to compositions for delivering carbon monoxide (CO) to cells using heme proteins as carriers. In one embodiment, the present invention relates to the use of MalPEG surface modified hemoglobin to deliver CO to cells.

BACKGROUND OF THE INVENTION

The delivery of oxygen in higher organisms is carried out by the protein hemoglobin. In mammals, hemoglobin has a molecular weight of approximately 64,000 Da and is composed of about 6% heme and 94% globin. Heine is a type of porphyrin molecule that coordinates to Fe(II) using its four nitrogen atoms as electron-pair donors. In coordination with globin (i.e. the globular polypeptide portion of hemoglobin), the heme binds $O_2$, and can also bind NO and CO. In its native form, mammalian hemoglobin contains four subunits (i.e., it is a tetramer), each containing a heme group and a globin polypeptide chain. In other animals, the structure of hemoglobin is somewhat different. For example, insects have dimeric hemoglobin consisting of only two heme groups and two globin chains. In contrast, other organisms such as annelids (such as earthworms) have giant hemoglobins consisting of over 100 heme-globin complexes. Mammals also have a monomeric heme protein called myoglobin, which is found mainly in muscle tissue where it serves as an intracellular storage site for oxygen.

In mammals, hemoglobin is found in red blood cells. Interestingly, free hemoglobin in the bloodstream is actually harmful, because of its vasoactivity. The vasoactivity of substances in the bloodstream can take the form of either vasoconstriction or vasodilation. Vasodilation is a physical change in a blood vessel, which results in an increased blood capacity through the blood vessel; and leads to decreased resistance and increased flow through the vessel. Vasodilation can either be active vasodilation or passive vasodilation. Active vasodilation is caused by a decrease in the tonus of smooth muscle in the wall of the vessel, whereas passive vasodilation is caused by increased pressure in the lumen of the vessel.

Pulmonary hypertension is a condition that commonly benefits from the use of vasodilators. Pulmonary hypertension results from an elevation of pulmonary arterial pressure over normal levels. For an adult human, a typical mean pulmonary arterial pressure is approximately 12-15 mm Hg. Pulmonary hypertension is said to exist when the pulmonary arterial pressure increases by at least 5 to 10 mm Hg over normal levels.

One form of pulmonary hypertension is hypoxia-induced pulmonary hypertension. Other examples include pulmonary hypertension resulting from disease states such as interstitial lung diseases with fibrosis, e.g., sarcoidosis and puemoconioses. Pulmonary hypertension can also result from emboli, from parasitic diseases such as shistosomiasis or filariasis, from multiple pulmonary vasculature occlusion associated with sickle cell disease, from cardiac disease, and from ischemic and valvular heart disease.

Attempts have been made to treat pulmonary hypertension by administering drugs with known systemic vasodilatory effects, such as calcium channel blockers, hydralazine, and nitroprusside. Although these drugs may be successful in lowering the pulmonary blood pressure, they typically also decrease systemic blood pressure, which may result in dangerous pooling of the blood in the venous circulation. This can lead to hypotension, ischemia and consequent heart failure.

Nitric oxide (NO) is one compound that plays an important role in regulating pulmonary blood flow. This vasodilator activates guanylate cyclase in pulmonary vascular muscle cells, with a subsequent increase in cyclic guanosine monophosphate and a decrease in intracellular calcium, leading to smooth muscle relaxation. Experimental studies on the physiological effects of NO have been facilitated by the development of a wide variety of organic compounds that spontaneously release NO and can be easily acquired to reproduce a physiological or pathophysiological function of NO.

Carbon monoxide (CO) also functions as a vasodilator. CO is a colorless, odorless and tasteless gas which is formed in many chemical reactions and in the thermal or incomplete decomposition of many organic materials. In the atmosphere, the average global levels are estimated to be 0.19 parts per million (p.p.m.), 90% of which comes from natural sources including ocean microorganism production, and 10% of which is generated by human activity. Thus, inhalation of even small quantities of CO is inevitable for living organisms.

The use of CO as a therapeutic agent has been explored. For example, Beutler administered CO as an inhalant at a concentration of 1000-2000 PPM to two patients suffering from Sickle Cell Disease. In both patients, anti-sickling was observed (E. Beutler, Blood 46:253-259 (1975). In addition, the effects of CO inhalation in a lung ischemia/reperfusion model were studied and shown to confer a benefit (C. Thiemermann, Nature Medicine 7:535-536 (2001)). However, in both studies, it was concluded that the dangers of CO inhalation outweighed the benefits. Thus, more recently, a carrier for CO has been proposed—U.S. Patent Publication No. 2003/0064114 describes the therapeutic delivery of carbon monoxide by metal carbonyls to enhance vasodilation.

In the body, CO is the product of metabolic breakdown of heme by heme oxygenase. Since all higher organisms use heme proteins for oxygen transport, CO itself is ubiquitous. CO binds to hemoglobin at the heme iron site with an affinity about 250 times higher than that of $O_2$ (J. W. Severinghaus, et al., "Oxygen Dissociation Curve Analysis at 98.7%-99.6% Saturation", in "Oxygen Affinity of Hemoglobin and Red Cell Acid Base Status", P. Astrup and M. Rorth, Eds., Academic Press, New York, N.Y. (1972)). CO can also bind to myoglobin with a very high affinity. The fact that CO is not converted to $CO_2$, and is instead eliminated from the body as CO, was established over 25 years ago (F. J. W. Roughton, Am. 3. Physiol. 145:239-252 (1945)). Because of its high affinity for CO, the hemoglobin molecule switches to its high affinity form (i.e. the relaxed or "R" form) at very low CO saturation levels, which effectively increases its affinity for $O_2$. This effect is the presumed basis for the favorable effect of CO on reversing sickled cells in Sickle Cell Disease (E. Beutler, Blood, 46:253-255 (1975)).

CO shares some of the biological effects of NO, the endothelium-derived vasodilator. Thus, CO also induces cyclic GMP (cGMP) synthesis by activation of soluble guanylate cyclase (sGC). In addition to activation of sGC, CO promotes vasorelaxation through mechanisms that involve stimulation of calcium-activated potassium channels or diminished synthesis of constrictor mediators, such as endothelin and 20-HETE (F. Zhang, et al., Am. J. Hypertens. 14:62S-67S (2001)). Recent studies have indicated that CO can reduce restenosis when administered prior to angioplasty, suppress endothelial cell apoptosis, reduce xenotransplant rejection, and reduce hypoxia-induced vasoconstriction. (See L. E. Otterbein, et al., Nat. Med. 9:183-190 (2003); S. Brouard, et al., J. Exp. Med. 192:1015-1026 (2000); Y. Lin, et al., J. Immunol. 164:4883-4892 (2001); and R. J. Gonzales, et al., Am. J. Physiol. Heart Circ. Physiol. 282:H30-H37 (2002)).

While the use of CO in clinical applications appears to be promising, its administration must be carefully controlled, since it is a poison. COHb levels of 16% predictably cause clinical symptoms, and as little as 10% can cause headaches. Levels of 70% are associated with seizures. Levels of as little as 5-10% can cause exertional angina in patients with underlying cardiovascular disease.

Accordingly, there is a need to develop carriers for delivering vasodilators such as NO and CO as therapeutic agents that facilitate controlled administration so that a clinical benefit can be achieved without the risk of toxicity or undesirable side effects. The present invention relates to the use of heme proteins such as hemoglobin as just such a carrier.

SUMMARY OF THE INVENTION

The present invention relates to compositions and methods for delivering CO or NO to cells. The method is performed by first preparing a CO- or NO-hemoglobin (Hb) complex; and thereafter contacting the cells with the XO-Hb complex. The Hb may be modified, such as by surface modification with, for example, maleimidyl-activated polyethylene glycol (MalPEG).

In one embodiment, the CO- and NO-Hb complexes are formed by first preparing an aqueous solution of Hb, and thereafter introducing gasous NO or CO into the solution. The Hb may previously be modified to block free sulfhydryl groups, which may involve mixing the Hb with an excess amount of MalPEG to form surface modified Hb, or MalPEG-Hb.

The compositions of the present invention comprise the CO- or NO-Hb complexes as described above in a pharmaceutically acceptable carrier, which is usually adapted for administration to a mammal.

The compositions are useful for preventing and treating a variety of different conditions known to involve CO and NO metabolism, such as: hypertension, radiation damage, endotoxic shock, inflammation, autoimmune diseases (e.g., rheumatoid arthritis), vascular restenosis, sickle cell disease, apoptosis, xenotransplant rejection, Alzheimer's Disease, hypoxia, hyperoxia-induced injury, cancer, transplant rejection, post-operative ileus, arteriosclerosis, post-ischemic organ damage, myocardial infarction, angina, hemorrhagic shock, sepsis, penile erectile dysfunction, adult respiratory distress syndrome, hepatic cirrhosis, cardiac hypertrophy, heart failure, ulcerative colitis, and stroke.

Other aspects of the invention are described throughout the specification and claims.

DETAILED DESCRIPTION OF THE INVENTION

Figure 1:
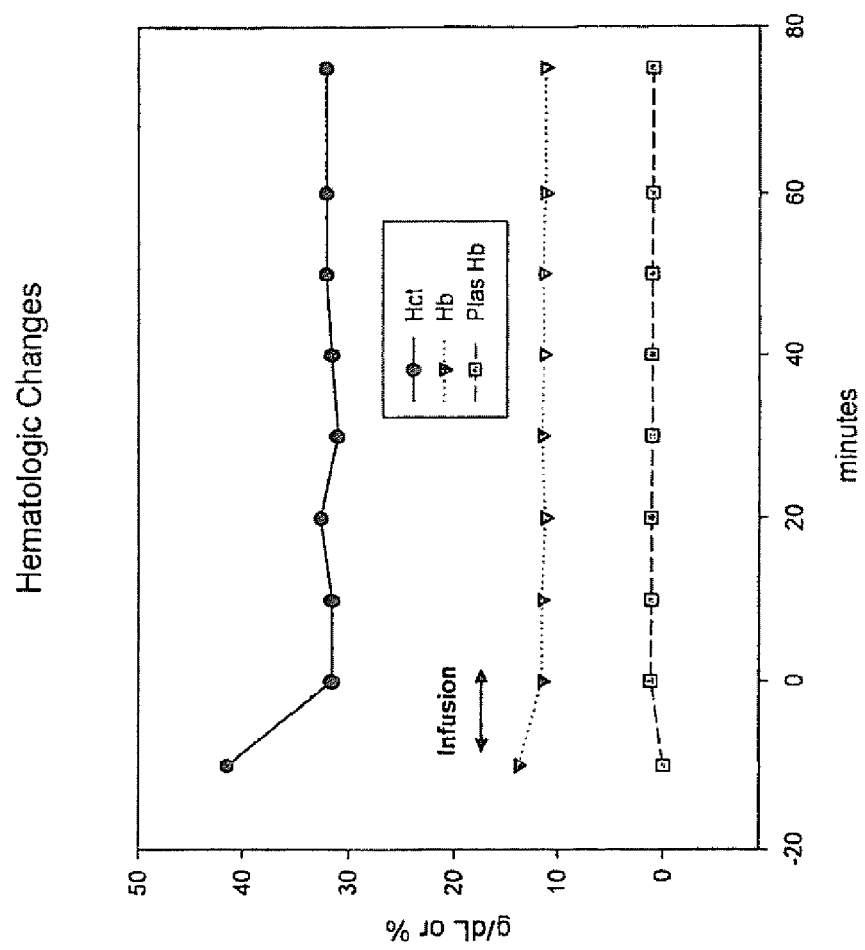
FIG. 1 depicts the hematologic changes after infusion of an exemplary composition, COMP4; hematocrit (Hct), total hemoglobin (Hb) and plasma hemoglobin (Plas Hb).

The present invention relates to compositions and methods for delivering nitric oxide (NO) or carbon monoxide (CO) to red blood cells or tissue using heme proteins as carriers. In one embodiment, the present invention relates to the use of modified hemoglobin to deliver NO or CO to red blood cells.

Definitions

To facilitate understanding of the invention set forth in the disclosure that follows, a number of terms are defined below.

The term "hemoglobin", or "heme protein", refers to any heme-containing protein complex that carries $O_2$, CO or NO as a ligand in coordination with the pendant groups on the heme Fe(II) and surrounding amino acids. As such, it includes tetrameric mammalian hemoglobin, dimeric insect hemoglobin, multimeric annelid hemoglobin, and myoglobin, as well as synthetically or recombinantly produced polypeptides or proteins.

The term "modified hemoglobin" refers to hemoglobin altered by a chemical reaction such as intra- and inter-molecular cross-linking, genetic manipulation, polymerization, encapsulation, and/or conjugation to other chemical groups (e.g., polyalkylene oxides, for example polyethylene glycol) or other adducts such as proteins, peptides, carbohydrates, synthetic polymers and the like. In essence, hemoglobin is "modified" if any of its structural or functional properties have been altered from its native state. As used herein, the term "hemoglobin" by itself refers both to native (unmodified) hemoglobin, as well as modified hemoglobin.

The term "surface-modified hemoglobin" is used to refer to hemoglobin described above to which chemical groups such as dextran or polyalkylene oxide have been attached, most usually covalently.

The term "stroma-free hemoglobin" (SFH) refers to hemoglobin from which all red blood cell membranes have been removed.

The term "methemoglobin" refers to an oxidized form of hemoglobin that contains iron in the ferric state (FeIII) and cannot function as an oxygen carrier.

The term "MalPEG-Hb" refers to hemoglobin to which malemidyl-activated PEG has been conjugated. Such MalPEG-Hb conjugates may be referred to by the following formula:

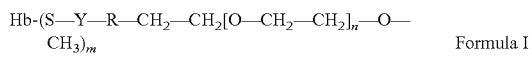
$$Hb\text{-}(S\text{-}Y\text{-}R\text{-}CH_2\text{-}CH_2[O\text{-}CH_2\text{-}CH_2]_n\text{-}O\text{-}CH_3)_m \quad \text{Formula I}$$

where Hb refers to tetrameric hemoglobin, S is a surface thiol group, Y is the succinimido covalent link between Hb and Mal-PEG, R is either absent or is alkyl, amide, carbamate or phenyl group (depending on the source of raw material and the method of chemical synthesis), $[O\text{-}CH_2\text{-}CH_2]_n$ are the oxyethylene units making up the backbone of the PEG polymer, where n defines the length of the polymer (e.g., MW=5000), and $O\text{-}CH_3$ is the terminal methoxy group.

The term "oxygen carrying capacity," or simply "oxygen capacity" refers to the capacity of hemoglobin to carry oxygen, but does not necessarily correlate with the efficiency in which it delivers oxygen. Oxygen carrying capacity is generally calculated from hemoglobin concentration, since it is known that each gram of hemoglobin binds 1.34 ml of oxygen. Thus, the hemoglobin concentration in g/dl multiplied by the factor 1.34 yields the oxygen capacity in ml/dl.

The term "ligand affinity" refers to the tightness in which hemoglobin binds ligands, such as $O_2$, NO and CO. This characteristic is usually defined by an equilibrium curve which relates the degree of saturation of hemoglobin molecules with ligands (Y axis) with the partial pressure of the ligand (X axis). The position of this curve is denoted by the value, P50, the partial pressure of the ligand at which the hemoglobin is half-saturated with the ligand, and is inversely related to ligand affinity. Hence the lower the P50, the higher the ligand affinity.

The terms "NO-heme protein complex" or "NO-Hb" and "CO-heme protein complex" or "CO-Hb" refer to the complex formed when NO or CO is substituted for $O_2$ as the ligand bound to heme. It does not include "nitrosylated hemoglobins", which are hemoglobins to which NO has been covalently attached to hemoglobin sulfhydryl groups.

The term "hemodynamic parameters" refers broadly to measurements indicative of blood pressure, flow and volume status, including measurements such as blood pressure, cardiac output, right atrial pressure, and left ventricular end diastolic pressure.

The term "mixture" refers to a mingling together of two or more substances without the occurrence of a reaction by which they would lose their individual properties; the term "solution" refers to a liquid mixture; the term "aqueous solution" refers to a solution that contains sonic water and may also contain one or more other liquid substances with water to form a multi-component solution; the term "approximately" refers to the actual value being within a range, e.g. 10%, of the indicated value.

The term "polyethylene glycol" refers to liquid or solid polymers of the general chemical formula $H(OCH_2CH_2)_n$ OH, or a derivative thereof, where n is greater than or equal to 4. Any PEG formulation, substituted or unsubstituted, can be used.

The term "polyakylene oxide" or "PAO" refers to a water-soluble polymer, such as PEG, wherein the alkyl repeating unit can be a two carbon group (as in PEG), a three carbon group, (as in polypropylene glycol), or other alkyl repeating group, or a block co-polymer of two or more different repeating units.

The term "vasodilation" refers to a physical change in a blood vessel, which results in an increased blood flow capacity through the blood vessel.

The meaning of other terminology used herein is easily understood by one of reasonable skill in the art.

Introduction

Molecular oxygen ($O_2$), carbon monoxide (CO), and nitric oxide (NO) are all diatomic oxygen-containing gases. As such, they share certain physical properties. However, their biological properties, while being somewhat overlapping, are different. In terms of the present invention, the focus is on the common property of CO and NO as vasodilators.

a. Nitric Oxide (NO)

Stroma free hemoglobin (SFH) causes vasoconstriction, which may lead to hypertension in animals and man (Amberson, W., Science 106:117-117 (1947); and Keipert, P., et al., Transfusion 33:701-708, (1993)). Human hemoglobin crosslinked between α chains with bis-dibromosalicyl-fumarate (ααHb) was developed by the U.S. Army as a model red cell substitute, but was abandoned by the Army after finding that it caused increases in pulmonary and systemic vascular resistance (Hess, J., et al. Blood 78:356A (1991)). A commercial version of this product was also abandoned after a disappointing Phase III clinical trial (Winslow, R. M., Vox sang 79:1-20 (2000).

One explanation for the vasoconstriction produced by SFH is that it readily binds NO, which is produced by the endothelium and functions as a vasodilator. In fact, recombinant hemoglobins with reduced affinity for NO have been produced which appear to be less hypertensive in top-load rat experiments (Doherty, D. H., et al., Nature Biotechnology 16:672-676 (1998); and Lemon, D. D., et al., Art. Cells, Blood Subs., and Immob. Biotech 24:378 (1996)). However, studies suggest that NO binding may not be the only explanation for the vasoactivity of hemoglobin. It has been found that PEG-Hb conjugates were virtually free of the hypertensive effect, even though their NO binding rates were identical to those of the severely hypertensive ααHb (Rohlfs, R. J., et. al., J. Biol. Chem. 273:12128-12134 (1998)). Accordingly, hemoglobins that have an affinity for NO should not all be presumed to be harmful.

At higher concentrations, NO and its derivatives have cytotoxic and mutagenic effects. For example, the interaction of NO with superoxide anions produces the reactive species, peroxynitrite, which is implicated in cell toxicity and neurodegenerative disorders. NO binding to heme proteins is also implicated in the activation and inhibition of various enzymes associated with pathophysiologies. Despite these well characterized potential deleterious effects of excess NO, it is known to have protective effects at appropriate concentrations. For example, low levels of NO may have a protective role against oxidative injury in acute inflammatory conditions. More importantly, its role as a vasodilator has been exploited in the design of many new small molecule-based therapeutics.

b. Carbon Monoxide (CO)

CO is produced as a byproduct of the breakdown of heme by enzymes located in the vessel wall (and elsewhere). Its role as a signaling molecule is implicated in the nervous, immune and cardiovascular systems. Like NO, the role of CO in vasodilation has also been explored in terms of designing new therapeutic agents to treat diseases and conditions associated with vasoconstriction.

Hemoglobin

The hemoglobin that is to be used in the practice of the present invention may be either native (unmodified); subsequently modified by a chemical reaction such as intra- or inter-molecular cross-linking, polymerization, or the addition of chemical groups (e.g., polyalkylene oxides, or other adducts); or it may be modified by recombinant engineering. Human alpha- and beta-globin genes have both been cloned and sequenced. Liebhaber, et al., P.N.A.S. 77:7054-7058 (1980); Marotta, et al., J. Biol. Chem. 353:5040-5053 (1977) (beta-globin cDNA). In addition, many recombinantly produced modified hemoglobins have now been produced using site-directed mutagenesis, although these "mutant" hemoglobin varieties were reported to have undesirably high oxygen affinities. See, e.g., Nagai, et al., P.N.A.S., 82:7252-7255 (1985).

The present invention is not limited by the source of the hemoglobin. For example, the hemoglobin may be derived from natural sources, such as from animal blood. Preferred sources of hemoglobin for certain applications are fish, amphibians, insects, reptiles, birds, nematodes, annelids, and mammals such as humans, cattle, swine, sheep, horses, monkeys, etc. In addition, hemoglobin may be produced by synthetic methods, including chemical synthesis and recombinant techniques.

Heme proteins that are not necessarily known in the literature as "hemoglobins" are also useful in the practice of the present invention and included in the use of the term "hemoglobin", as long as they bear heme moieties capable of interacting with the protein moiety and iron to bind CO and NO in a reversible fashion.

Hemoglobin Modifications

In an exemplary embodiment, the heme protein is modified hemoglobin. A preferred modification to hemoglobin is "surface-modification," i.e. covalent attachment of chemical groups to the exposed amino acid side chains on the hemoglobin molecule. Modification is carried out principally to increase the molecular size of the hemoglobin, most often by covalent attachment of polymeric moieties such as synthetic polymers, carbohydrates, proteins and the like. Generally, synthetic polymers are preferred.

Suitable synthetic hydrophilic polymers include, inter alia, polyalkylene oxide, such as polyethylene oxide ($(CH_2CH_2O)_n$), polypropylene oxide ($(CH(CH_3)CH_2O)_n$) or a polyethylene/polypropylene oxide copolymer ($(CH_2CH_2O)_n$—$(CH(CH_3)CH_2O)_n$). Other straight, branched chain and optionally substituted synthetic polymers that would be suitable in the practice of the present invention are well known in the medical field.

Most commonly, the chemical group attached to the hemoglobin is polyethylene glycol (PEG), because of its pharmaceutical acceptability and commercial availability. PEGs are polymers of the general chemical formula $H(OCH_2CH_2)_nOH$, where n is generally greater than or equal to 4. PEG formulations are usually followed by a number that corresponds to their average molecular weight. For example, PEG-200 has an average molecular weight of 200 and may have a molecular weight range of 190-210. PEGs are commercially available in a number of different forms, and in many instances come preactivated and ready to conjugate to proteins.

The number of PEGs to be added to the hemoglobin molecule may vary, depending on the size of the PEG. However, the molecular size of the resultant modified hemoglobin should be sufficiently large to avoid being cleared by the kidneys to achieve the desired half-life. Blumenstein, et al., determined that this size is achieved above 84,000 molecular weight. (Blumenstein, et al., in "Blood Substitutes and Plasma Expanders," Alan R. Liss, editors, New York, N.Y., pages 205-212 (1978).) Therein, the authors conjugated hemoglobin to dextran of varying molecular weight. They reported that a conjugate of hemoglobin (with a molecular weight of 64,000) and dextran (having a molecular weight of 20,000) "was cleared slowly from the circulation and negligibly through the kidneys," but increasing the molecular weight above 84,000 did not alter the clearance curves. Accordingly, as determined by Blumenstein, et al., it is preferable that the modified hemoglobin have a molecular weight of at least 84,000.

In one embodiment of the present invention, the hemoglobin is modified with "MalPEG," which means hemoglobin to which malemidyl-activated PEG has been conjugated. See U.S. Pat. No. 6,844,317. Such MalPEG-Hb conjugates may be further referred to by the following formula:

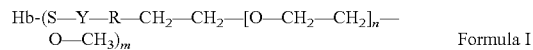

Hb-(S—Y—R—$CH_2$—$CH_2$—[O—$CH_2$—$CH_2$]$_n$—O—$CH_3$)$_m$      Formula I where Hb refers to hemoglobin, S is a surface thiol group, Y is the succinimido covalent link between Hb and MalPEG, R is either absent or is an alkyl, amide, carbamate or phenyl group (depending on the source of raw material and the method of chemical synthesis), [O—$CH_2$—$CH_2$]$_n$ are the oxyethylene units making up the backbone of the PEG polymer, where n defines the length of the polymer (e.g., MW=5000), and O—$CH_3$ is the terminal methoxy group. When R is alkyl, it may be straight chain or branched, substituted or unsubstituted, heteroatom-containing or heteroatom-free, saturated or unsaturated $C_1$, $C_2$, $C_3$, $C_4$, $C_5$ or $C_6$.

As described in U.S. Pat. No. 6,844,317, the MalPEG-Hb exists in a more relaxed or R-state that binds ligands more tightly-compared to native tetrameric hemoglobin. This results in higher ligand affinity and impaired cooperativity, which also facilitates ligand offloading (K. D. Vandegriff, et al, Biochemical J. 382:183-189 (2004)). Also described therein is the process of first "thiolating" the hemoglobin using a thiolation reaction to introduce additional sulfhydryl moieties.

Forming NO-Hb and CO-Hb Complexes

The NO- and CO-Hb complexes of the present invention can be formed using any known methods for forming oxyhemoglobin, simply by substituting NO or CO for $O_2$. This generally involves introducing a source of NO or CO to a solution of hemoglobin such that the hemoglobin becomes "liganded" with NO or CO instead of $O_2$ (K. D. Vandegriff, et al., Biochem. J. 382:183-189 (2004)). Since hemoglobin has a higher affinity for NO and CO than it does for $O_2$, it is not necessary to first deoxygenate the hemoglobin. Accordingly, the most convenient way of forming NO- and CO-Hb complexes is by introducing 100% gaseous NO or CO to a solution of hemoglobin.

It should be noted that hemoglobin to which ionic species of NO or CO are bound to the amino acid side groups in the globin chain are not NO- and CO-Hb complexes as defined herein, since such compounds do not contain diatomic (non-ionic) NO and CO as ligands in the heme pocket instead of $O_2$. For example, nitrosylhemoglobin is formed when native hemoglobin is exposed to a $NO^+$ donor under conditions that cause it to bind to free sulfhydryl groups (U.S. Pat. No.

6,627,738). Such nitrosylhemoglobins still carry $O_2$, whereas the NO- and CO-Hb complexes of the present invention do not. Furthermore, when the modified hemoglobin is formed by a reaction directed towards sulfhydryl moieties such as described above, these moieties are no longer available for NO or CO binding.

Formulation

The formulation of the CO- and NO-Hb complexes described herein as a pharmaceutical composition for the delivery of CO or NO typically comprises mixing them with a pharmaceutically acceptable carrier, such as an aqueous solution of salts, stabilizers and/or buffers that are known to be physiologically acceptable. Such carriers should necessarily be free of toxic compounds and infectious agents, as well as interfering substances, i.e. substances that would interfere with the ability of the compositions described herein to carry out their role of delivering CO or NO.

The precise formulation depends on the route of administration, which in the case of an injectable composition, will involve formulation in an aqueous solution as described above at a concentration of between, for example, 0.1-6 g/dL hemoglobin. However, different carriers may be used for alternate routes of administration, such as subcutaneous, nasal, oral, intramuscular, intraperitoneal and the like. All such formulation methods are routinely practiced by skilled clinicians and pharmacologists.

Suitable excipients to be included in aqueous carriers for injection include, for example, proteins, glycoproteins, polysaccharides, and other colloids, as well as crystalloids. It is not intended that these embodiments be limited to any particular diluent.

Uses

It is contemplated that the present invention and its embodiments will be useful for delivering CO or NO with a heme protein carrier (i.e. in the form of NO- or CO-Hb complexes) in a variety of different applications. It should be understood that heme proteins, and in particular mammalian hemoglobin, are perhaps the most well characterized class of proteins in existence. It should also be understood that CO and NO are alternative ligands to $O_2$, and thus heme proteins can be utilized to deliver these alternative ligands in the same manner as they are currently being developed and used for the delivery of $O_2$. For this reason, a skilled clinician could easily modify known methods of use to carry out the methods described herein using routine optimization.

The use of CO and NO as vasodilators is described in the literature. For example, the delivery of CO and NO by heme proteins according to the present invention can be used to promote vasodilation either locally or generally, inhibit platelet aggregation, stimulate neurotransmission, relax smooth muscles, etc.

In addition, CO- and NO-Hb complexes can be used, for example, for the purpose of preventing or treating conditions associated with vasoactivity, such as: hypertension, radiation damage, endotoxic shock, inflammation, autoimmune diseases (e.g., rheumatoid arthritis), vascular restenosis, sickle cell disease, apoptosis, xenotransplant rejection, Alzheimer's Disease, hypoxia, hyperoxia-induced injury, cancer, transplant rejection, post-operative ileus, arteriosclerosis, post-ischemic organ damage, myocardial infarction, angina, hemorrhagic shock, sepsis, penile erectile dysfunction, adult respiratory distress syndrome, hepatic cirrhosis, cardiac hypertrophy, heart failure, ulcerative colitis and stroke.

In addition to such clinical uses, the CO- and NO-Hb complexes of the present invention are useful in delivering CO or NO to red blood cells (RBCs), which can thereafter be administered for clinical purposes. More particularly, the CO- and NO-Hb complex can be mixed with RBCs, which leads to an exchange of CO and NO between the complex and the intracellular hemoglobin.

Administration

As described above, typical routes of administration include, for example, intraveneous, subcutaneous, nasal, oral, intramuscular, intraperitoneal and the like, which necessarily involve different routine formulation techniques.

The dosage amount is easily established based on the teachings herein, and is ordinarily a prophylactically effective amount or a therapeutically effective amount as determined by routine optimization. The precise dosage volume, concentration and frequency of administration can also be established based on observation of physiological and other changes, which is well within the control of the administering physician

EXPERIMENTS

Experiment 1

In vitro Mixtures of COMP4 and Red Blood Cells

In this experiment, MP4 (human hemoglobin modified with maleimide-PEG 5000 prepared according to U.S. Pat. No. 6,844,317) was equilibrated with 100% CO and mixed in various proportions with fresh human blood (see Table 1). After 30 minutes at room temperature, the cells and plasma were separated by centrifugation and the percent CO hemoglobin in each was determined using a Co-Oximeter. In each case, the saturation of CO in red blood cells increased and the CO saturation in MP4 decreased, indicating a net transfer of CO from MP4 to red blood cells

TABLE 1

| | | Before Mixing | | | | | After Mixing | | | | |
|---|---|---|---|---|---|---|---|---|---|---|---|
| | | RBC | | | MP4 | | | RBC | MP4 | Coservation of CO | |
| | | Hb | COHb | vol | Hb | COHb | vol | COHb | COHb | (mL × conc × % CO) | |
| Expt | | (g/dL) | (%) | (mL) | (g/dL) | (%) | (mL) | (%) | (%) | start | end |
| 1 | | 17.4 | 1,7 | 4 | 4.5 | 92.6 | 1 | 6.9 | 2.8 | rbc CO 118.3 | 480.2 |
| | | | | | | | | | | MP4 CO 416.7 | 12.6 |
| | | | | | | | | | | Total CO 535.0 | 492.8 |

TABLE 1-continued

| | Before Mixing | | | | | | After Mixing | | Coservation of CO | | |
|---|---|---|---|---|---|---|---|---|---|---|---|
| | RBC | | | MP4 | | | RBC | MP4 | | | |
| | Hb | COHb | vol | Hb | COHb | vol | COHb | COHb | (mL × conc × % CO) | | |
| Expt | (g/dL) | (%) | (mL) | (g/dL) | (%) | (mL) | (%) | (%) | | start | end |
| 2 | 17.4 | 1.7 | 4 | 4.5 | 92.6 | 2 | 12.4 | 6.7 | rbc CO | 118.3 | 863.0 |
| | | | | | | | | | MP4 CO | 833.4 | 60.3 |
| | | | | | | | | | Total CO | 951.7 | 923.3 |
| 3 | 17.4 | 1.7 | 4 | 4.5 | 92.6 | 4 | 22.4 | 15.6 | rbc CO | 118.3 | 1559.0 |
| | | | | | | | | | MP4 CO | 1666.8 | 280.8 |
| | | | | | | | | | Total CO | 1785.1 | 1839.8 |

In a variant of this experiment, red blood cells were equilibrated with 100% CO and mixed in various proportions with MP4 (see Table 2). The total amount of CO in the mixture was much greater in this experiment because of the higher concentration of hemoglobin in the red blood cells, but once again CO can be seen to redistribute from the red blood cells to the MP4 during the incubation period.

TABLE 2

| | Before Mixing | | | | | | After Mixing | | Coservation of CO | | |
|---|---|---|---|---|---|---|---|---|---|---|---|
| | RBC | | | MP4 | | | RBC | MP4 | | | |
| | Hb | COHb | vol | Hb | COHb | vol | COHb | COHb | (mL × conc × % CO) | | |
| Expt | (g/dL) | (%) | (mL) | (g/dL) | (%) | (mL) | (%) | (%) | | start | end |
| 1 | 17.2 | 90.4 | 2 | 4.1 | 0 | 0.5 | 98.7 | 76.7 | rbc CO | 3110 | 3395 |
| | | | | | | | | | MP4 CO | 0 | 157 |
| | | | | | | | | | Total CO | 3110 | 3553 |
| 2 | 17.2 | 90.4 | 2 | 4.1 | 0 | 1 | 83.7 | 73.4 | rbc CO | 3110 | 2879 |
| | | | | | | | | | MP4 CO | 0 | 301 |
| | | | | | | | | | Total CO | 3110 | 3180 |
| 3 | 17.2 | 90.4 | 2 | 4.1 | 0 | 2 | 76.6 | 67.4 | rbc CO | 3110 | 2635 |
| | | | | | | | | | MP4 CO | 0 | 553 |
| | | | | | | | | | Total CO | 3110 | 3188 |
| 4 | 17.2 | 90.4 | 4 | 4.1 | 0 | 4 | 65.7 | 57.6 | rbc CO | 6220 | 4520 |
| | | | | | | | | | MP4 CO | 0 | 945 |
| | | | | | | | | | Total CO | 6220 | 5465 |

Mass balance analysis in both of these experiments confirms that the total amount of CO is conserved. That is, there is no degradation to some metabolite. Of particular interest, both of these studies show that the affinities of MP4 and red blood cells are very similar, producing levels of saturation, at equilibrium, that are nearly the same.

Experiment 2

20% Topload Infusion of COMP4 in the Rat

Figure 2:
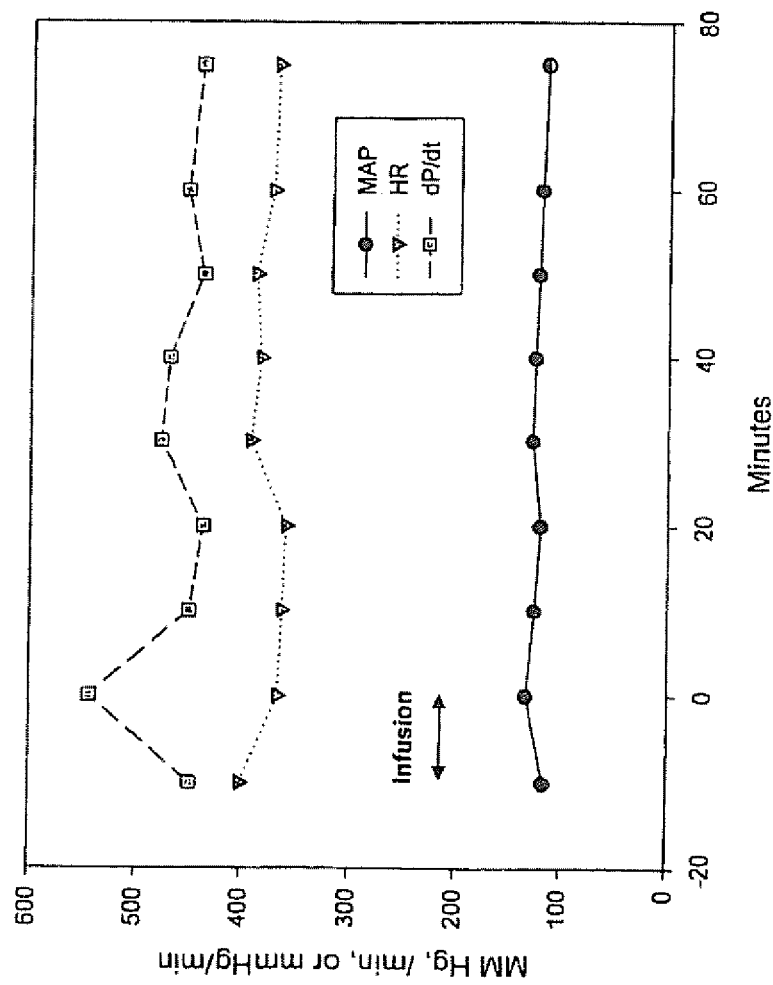
FIG. 2 depicts the hemodynamic changes after infusion of COMP4; mean arterial pressure (MAP), heart rate (HR), and cardiac contraction force (dP/dt).
Figure 3:
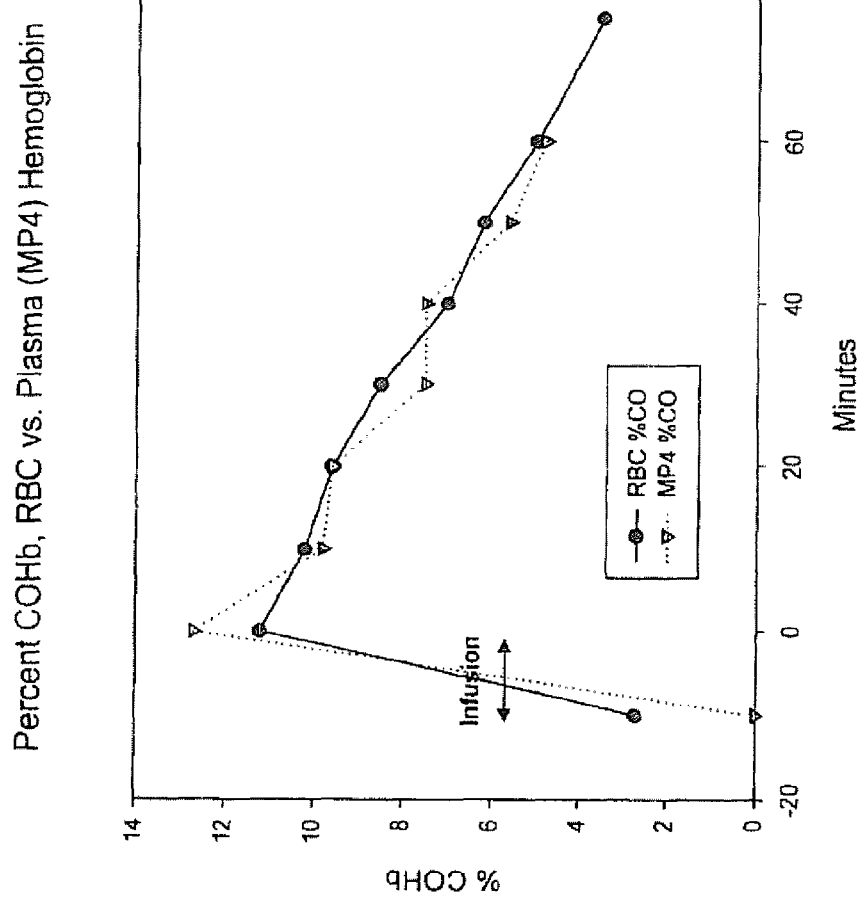
FIG. 3 depicts the changes in percent COHb in RBCs and plasma after infusion of COMP4.

To test the overall toxicity of COMP4 in the rat, a topload infusion of 20% of estimated blood volume was carried out at 2 mL/minute. Given the size of the animals in this study, the infusion was complete in approximately 7 minutes. FIG. 1 shows a fall in hematocrit that is predicted by the expansion of the blood volume and dilution of the red cell mass. After infusion, however, there is no further change in hematocrit, indicating that the blood volume is stable. The hemodynamic changes (FIG. 2) include an initial increase in the force of cardiac contraction (dP/dt), probably because of the expanded blood volume. Very little change in mean arterial pressure (MAP) or heart rate (HR) are seen. The percent COHb, in both the red blood cells and MP4 compartments (FIG. 3) are nearly identical, indicating that the redistribution of CO between the 2 compartments is almost instantaneous after the infusion, or that it is complete by the end of the topload period. In contrast, the loss of CO from both hemoglobin compartments takes place over about an hour, a significantly slower process. This figure also shows that the maximum level of COHb is approximately 12%, a level that is probably safe in healthy animals or humans.

Figure 4:
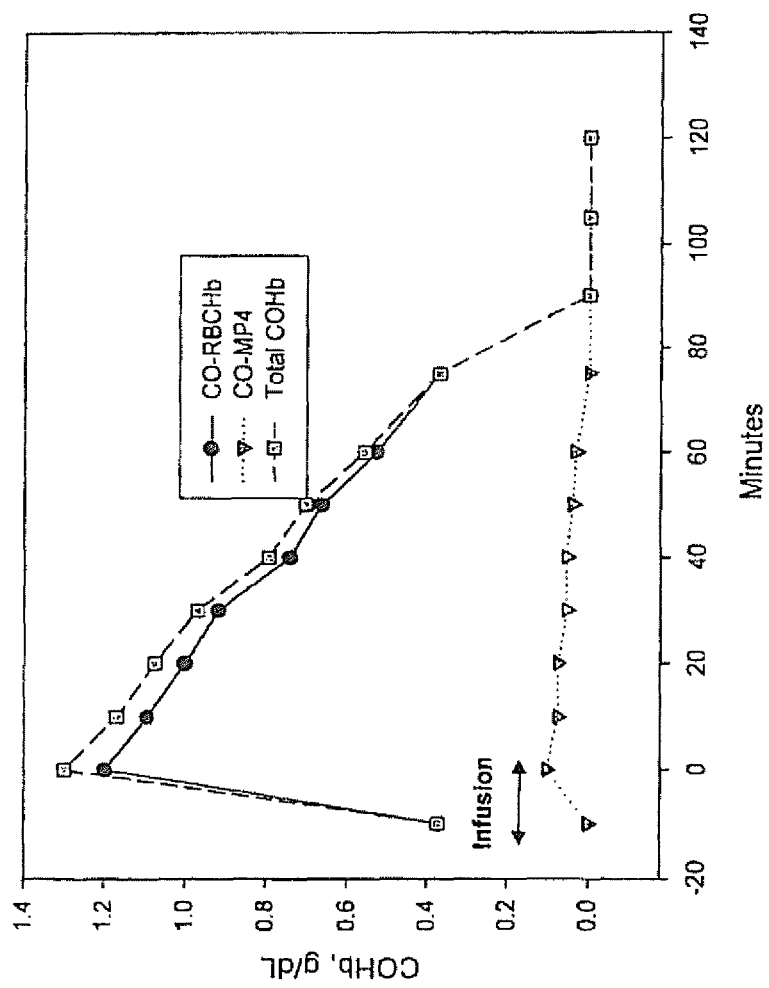
FIG. 4 depicts the changes in COHb concentration (g/dL) in RBCs, complexed to MP4, and total COHb.

The total amount of CO hemoglobin is shown in FIG. 4, showing that while the degree of saturation is similar in red cells and MP4 (FIG. 3), but bulk of the CO moves fro MP4 to red blood cells, which most likely explains why release from the vascular compartment is slow: diffusional movement of CO from red cells to tissue would likely be limited by the low solubility of CO in plasma.

This experiment confirms that the CO moves from MP4 to red blood cells very quickly but then is released to tissues much slower, with a half-time approaching 30 minutes. The experiment also shows there are no short term adverse effects on the cardiovascular system.

Experiment 3

50% Blood Volume Exchange Transfusion (ET) with COMP4 followed by 60% Blood Volume Controlled Hemorrhage In this experiment, rats are exchanged transfused at 0.5 mL/min with fully saturated COMP4. After a short rest period, a controlled hemorrhage of 60% of estimated blood volume is performed over one hour. Animals are observed for an additional hour, then euthanized if they survive. The control in this case is CO-saturated stroma free hemoglobin (CO-SFH). In addition to survival, the outcomes to be measured include the location of the CO, hemodynamics and acid-base balance.

Figure 5:
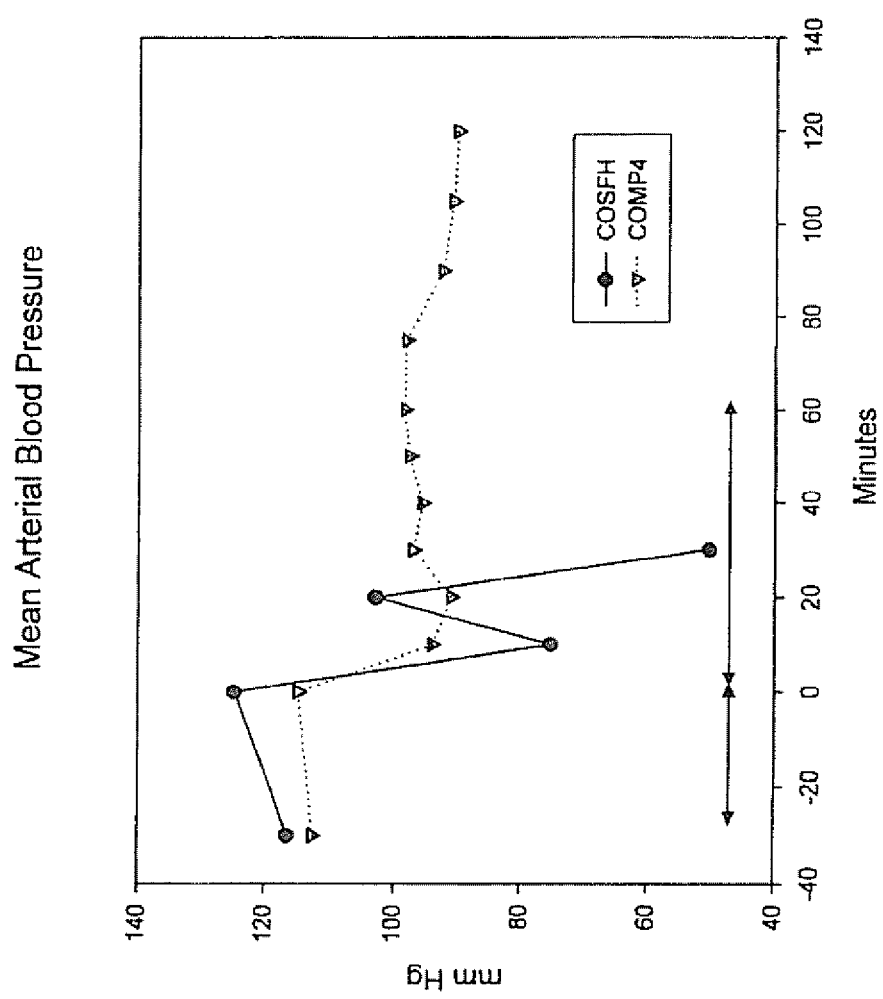
FIG. 5 depicts the changes in mean arterial blood pressure (mm Hg) after infusion of CO-SFH (stroma free hemoglobin) and COMP4.
Figure 6:
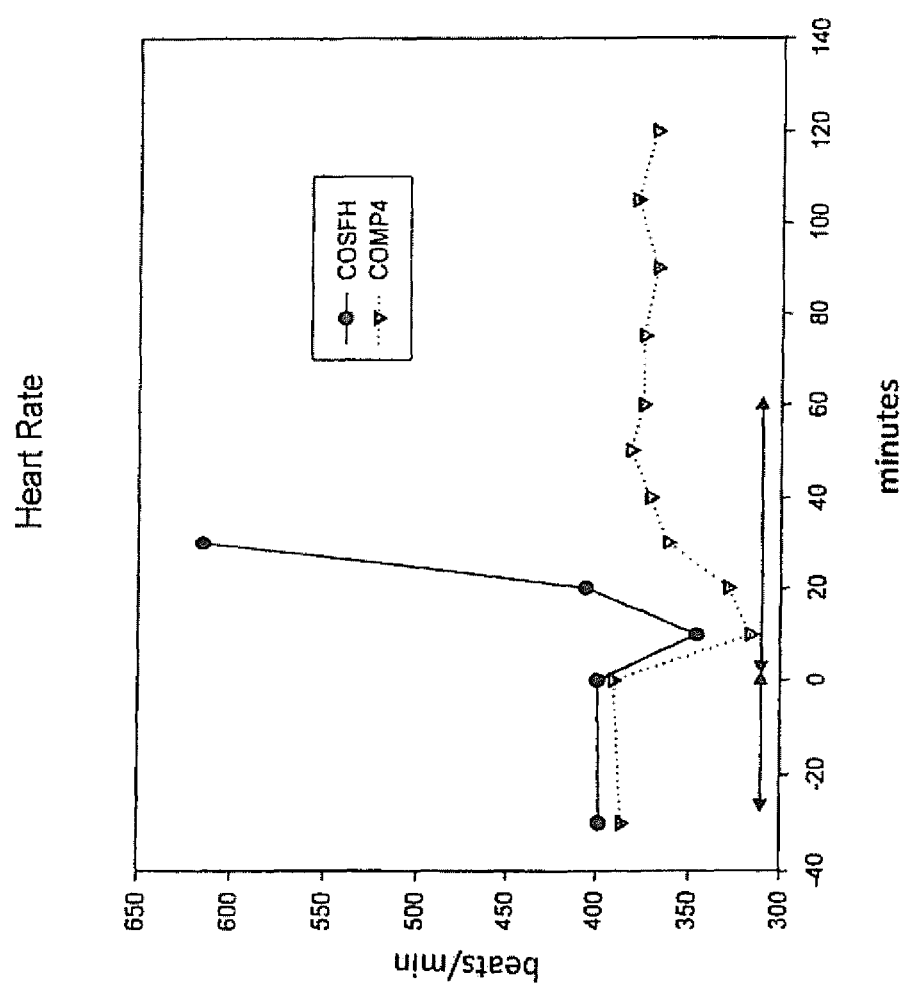
FIG. 6 depicts the changes in heart rate after infusion of CO-SFH and COMP4.
Figure 7:
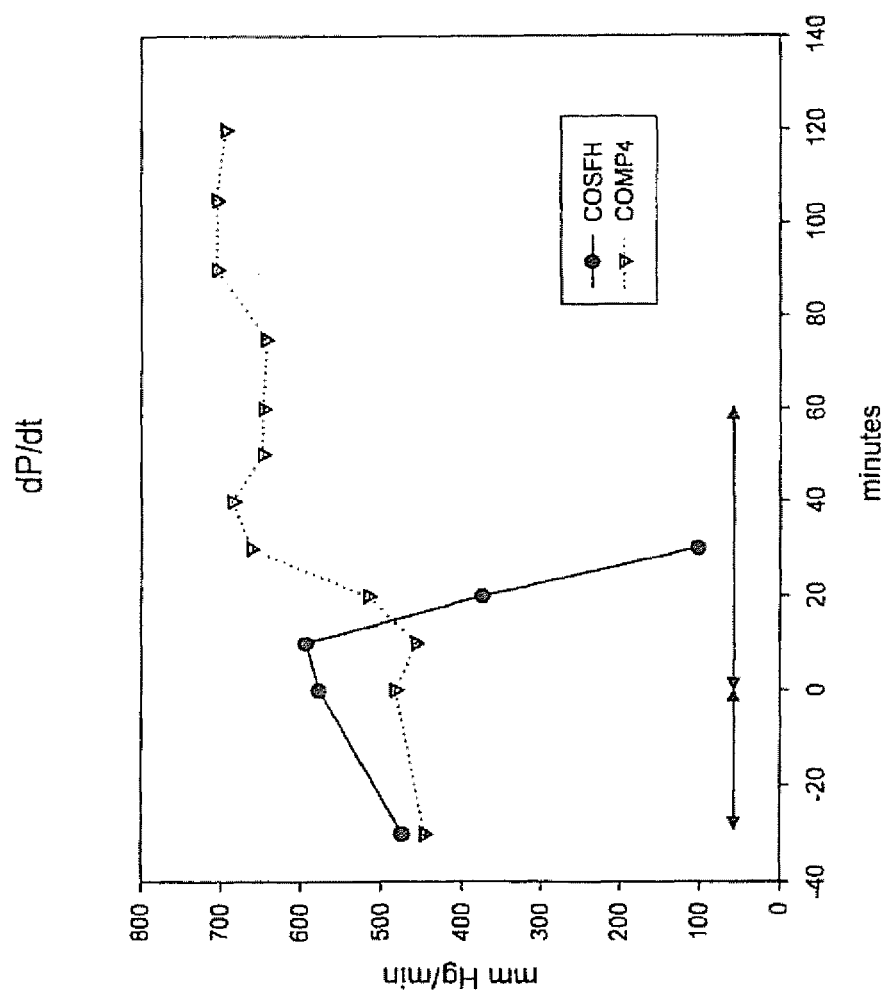
FIG. 7 depicts the changes in cardiac contraction force (dP/dt) after infusion of CO-SFH and COMP4.

The hemodynamic response to the COMP4 is similar to that seen with $O_2$-MP4 (FIG. 5). That is, a very small fall in mean arterial pressure during the initial stages of the hemorrhage, followed by a stabilization and eventual survival of the animal. In contrast, the animals infused with CO-SFH did not survive the hemorrhage period. The heart rate initially falls and then returns to baseline in the COMP4 animals but rose steadily in the CO-SFH animal until its death (FIG. 6). The force of myocardial contraction (FIG. 7) increased in both groups of animals, but fell rapidly in the CO-SFH animals until death.

Figure 8:
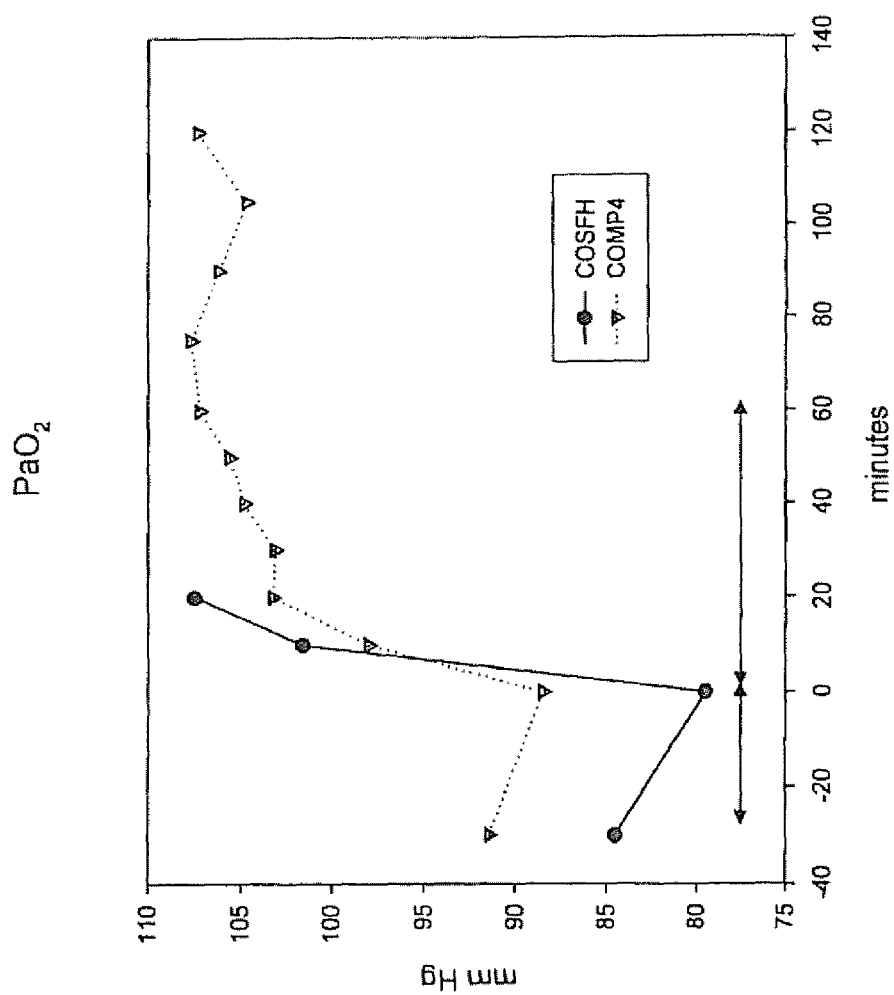
FIG. 8 depicts the changes in arterial $PO_2$ (mm Hg) after infusion of CO-SFH and COMP4.
Figure 9:
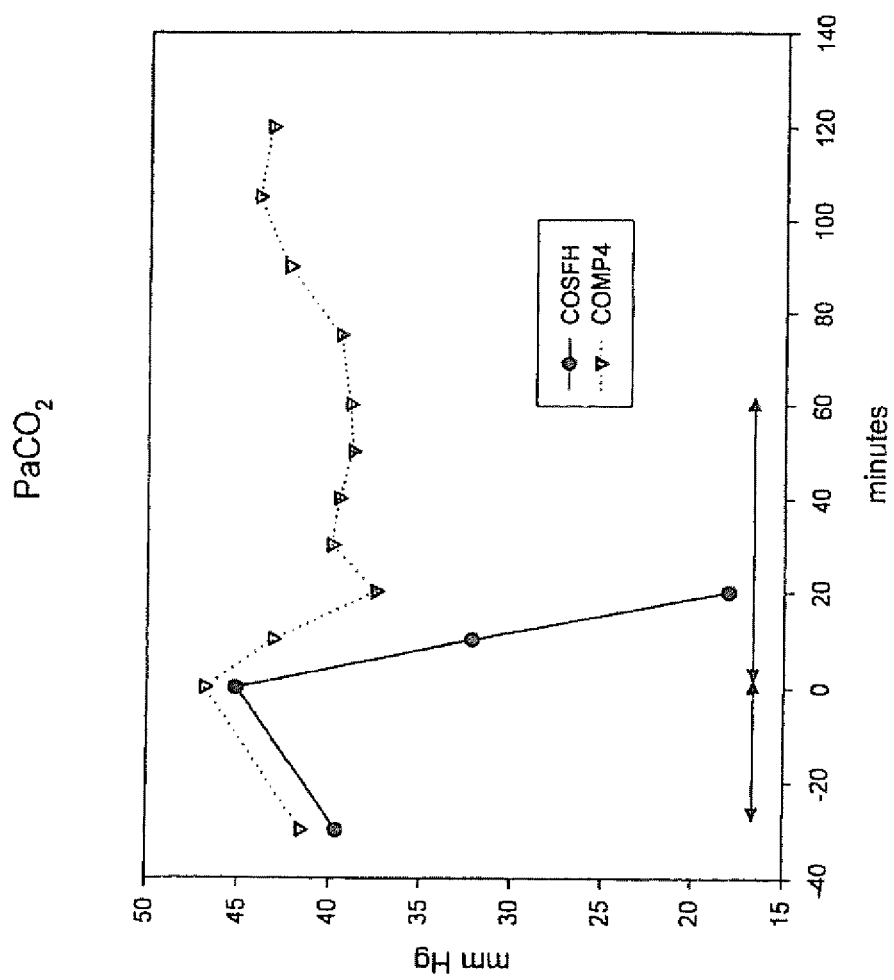
FIG. 9 depicts the changes in $PCO_2$ (mm Hg) after infusion of CO-SFH and COMP4.
Figure 10:
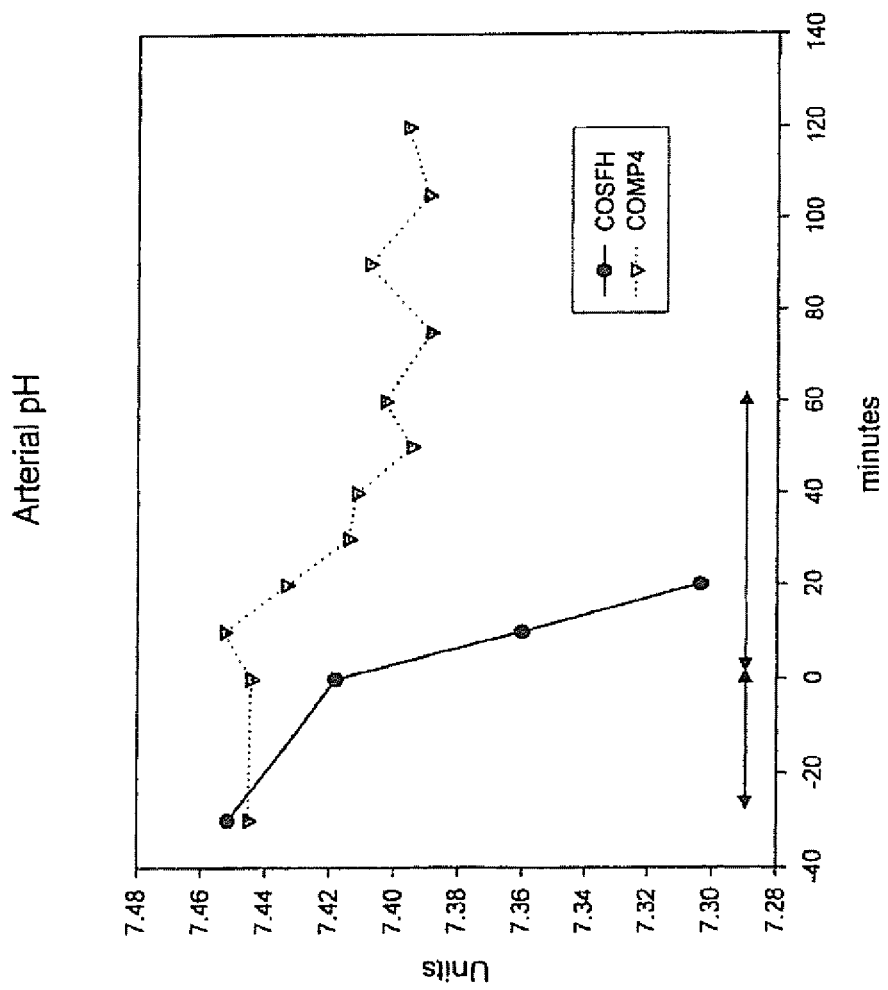
FIG. 10 depicts the changes in arterial pH after infusion of CO-SFH and COMP4.
Figure 11:
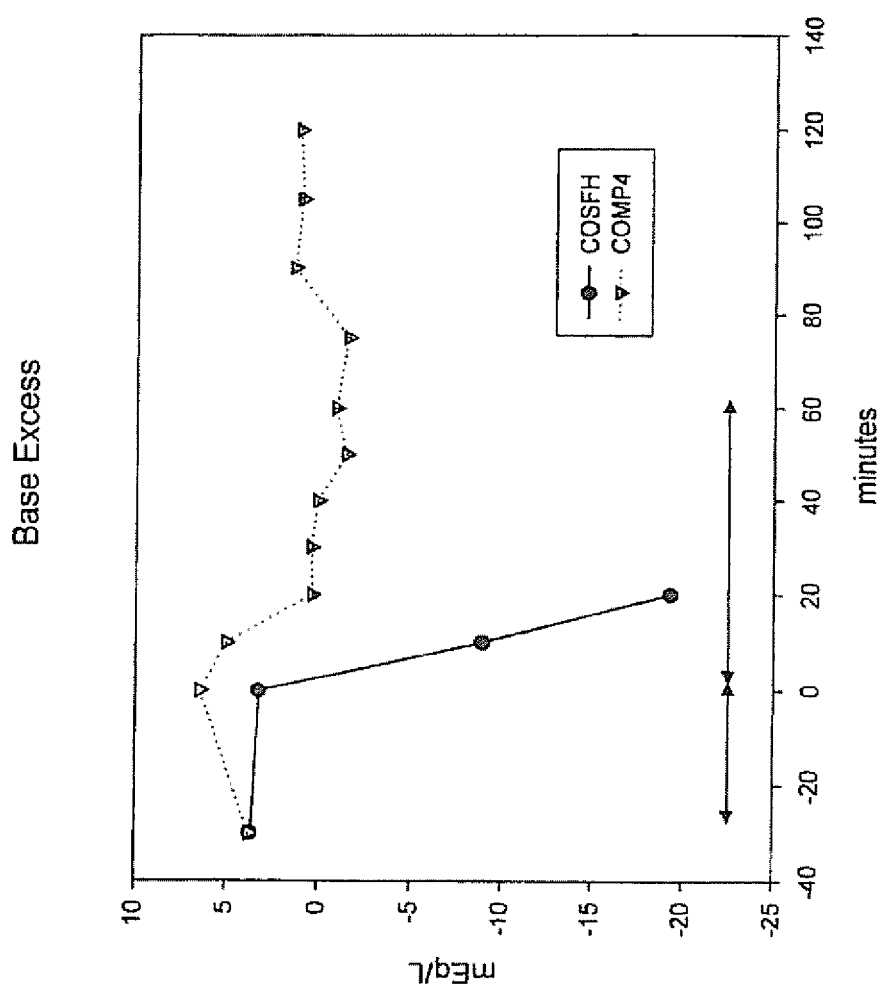
FIG. 11 depicts the changes in the acid-base balance as measured by excess base (mEq/L) after infusion of CO-SFH and COMP4.
Figure 12:
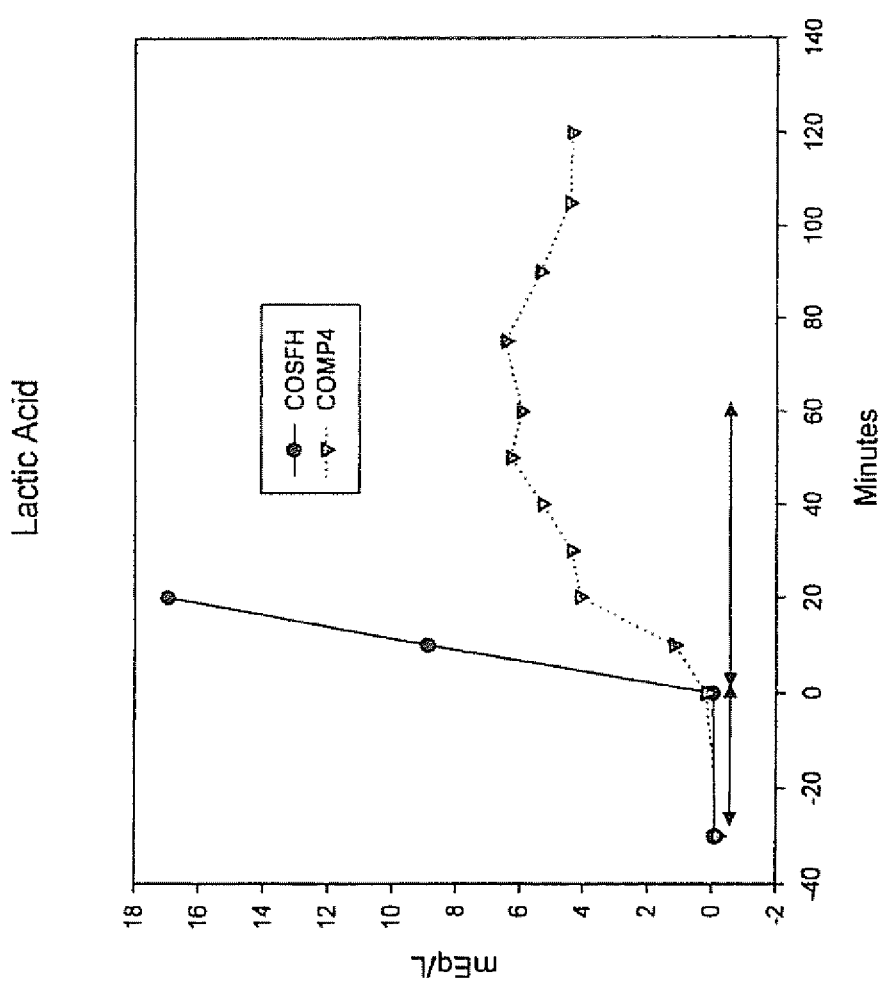
FIG. 12 depicts the changes in lactic acid (mEq/L) after infusion of CO-SFH and COMP4.

All animals increased arterial $PO_2$ (FIG. 8), an effect that is not completely due to hyperventilation because the arterial $PCO_2$ did not fall significantly in the COMP4 animals (FIG. 9). The fall in $PCO_2$ in the CO-SFH animals most likely indicates a fall in cardiac output. Arterial pH falls slightly in the COMP4 animals but dramatically in the CO-SFH animals (FIG. 10). Excellent overall acid-base balance in the COMP4 animals is indicated by well-controlled base excess (FIG. 11), whereas the base excess falls dramatically in the CO-SFH animals. Finally, inadequate $O_2$ delivery to tissues is confirmed by the rapid and irreversible accumulation of lactic acid in the CO-SFH animals compared to the pattern of recovery in the COMP4 animals (FIG. 12).

Figure 13:
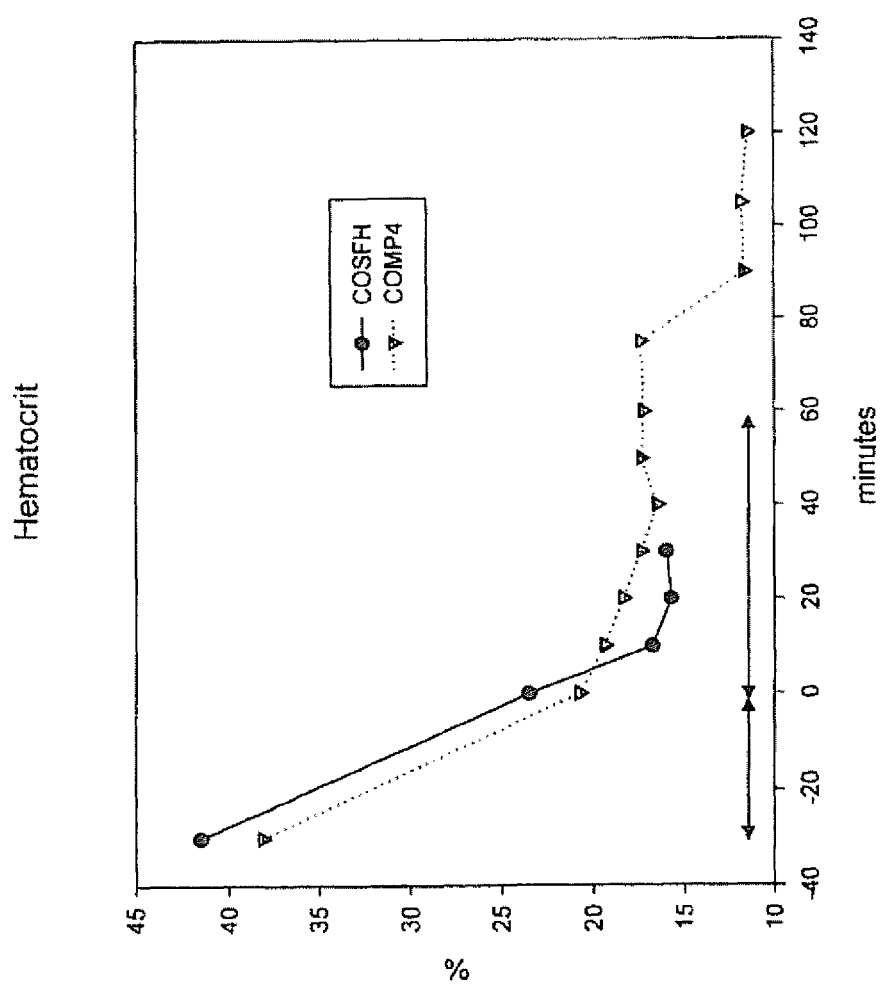
FIG. 13 depicts the changes in hematocrit after infusion of CO-SFH and COMP4.
Figure 14:
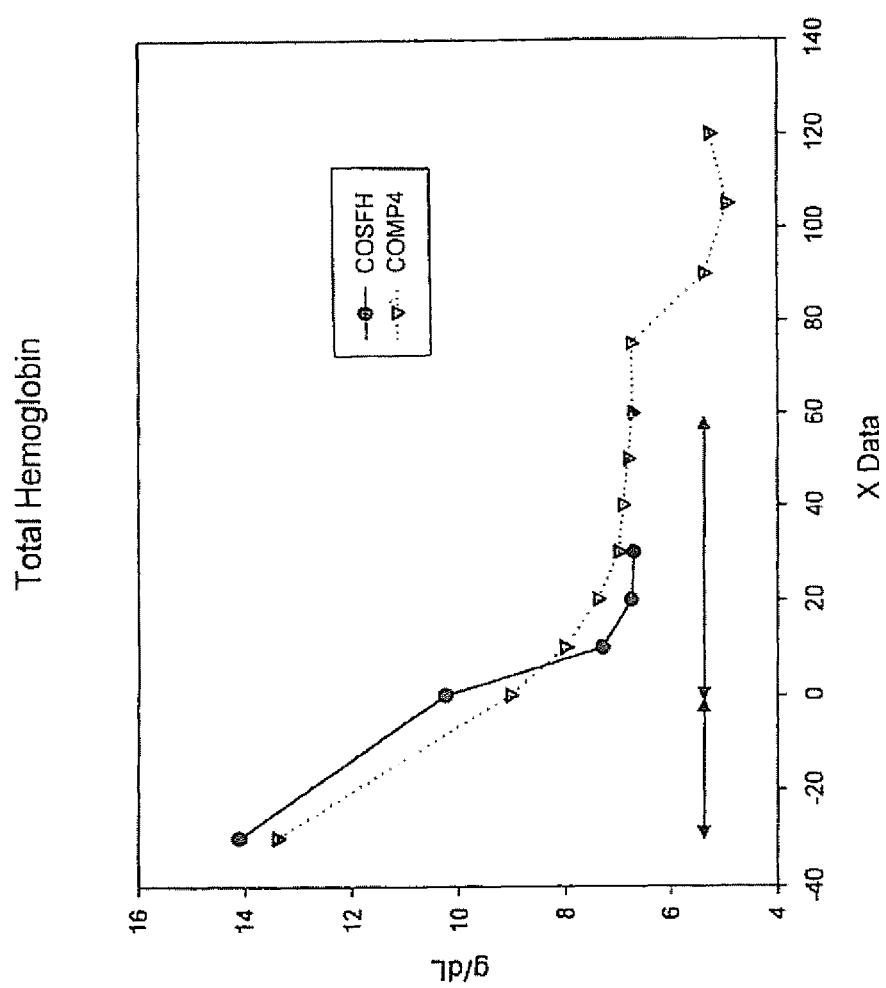
FIG. 14 depicts the changes in total hemoglobin concentration (g/dL) after infusion of CO-SFH and COMP4.
Figure 15:
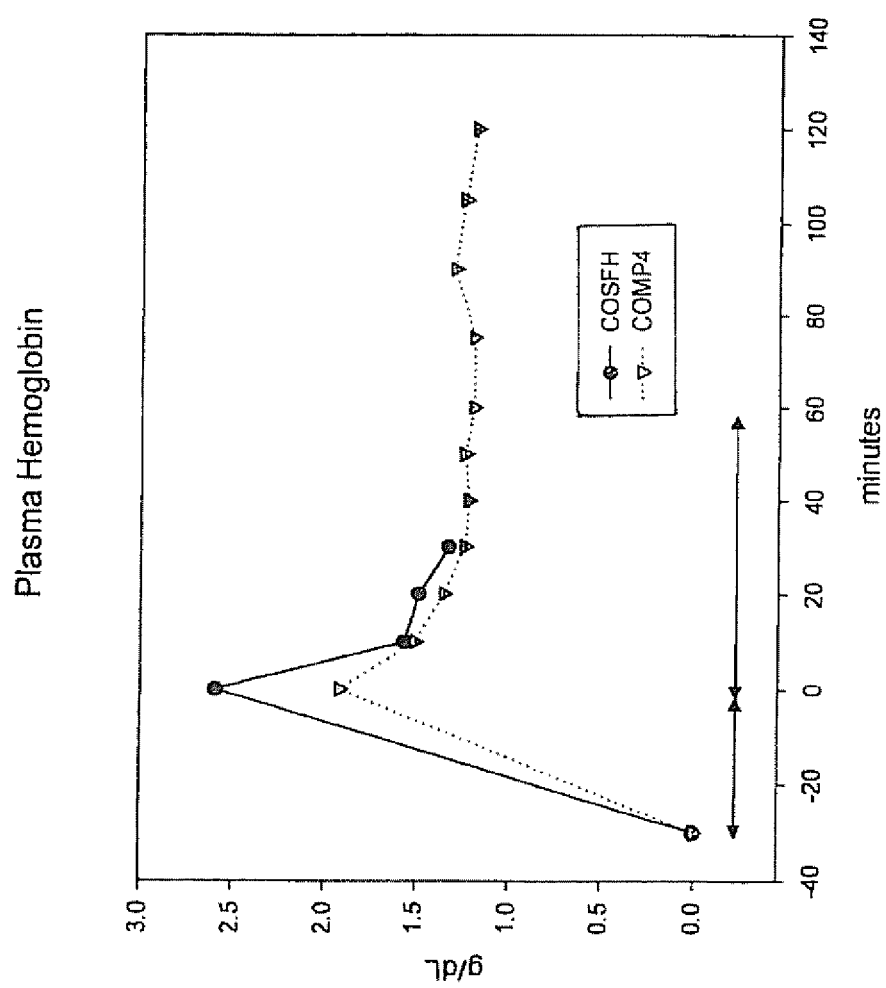
FIG. 15 depicts the changes in plasma hemoglobin concentration (g/dL) after infusion of CO-SFH and COMP4.
Figure 16:
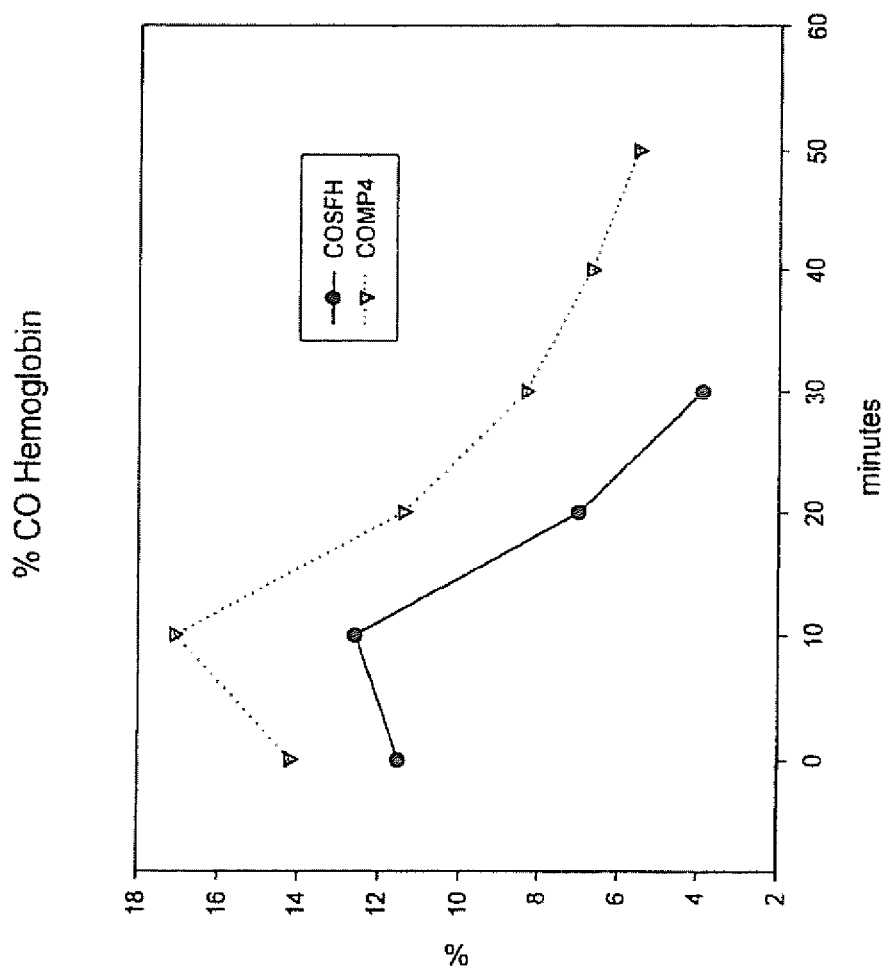
FIG. 16 depicts the changes in percent CO hemoglobin after infusion of CO-SFH and COMP4.
Figure 17:
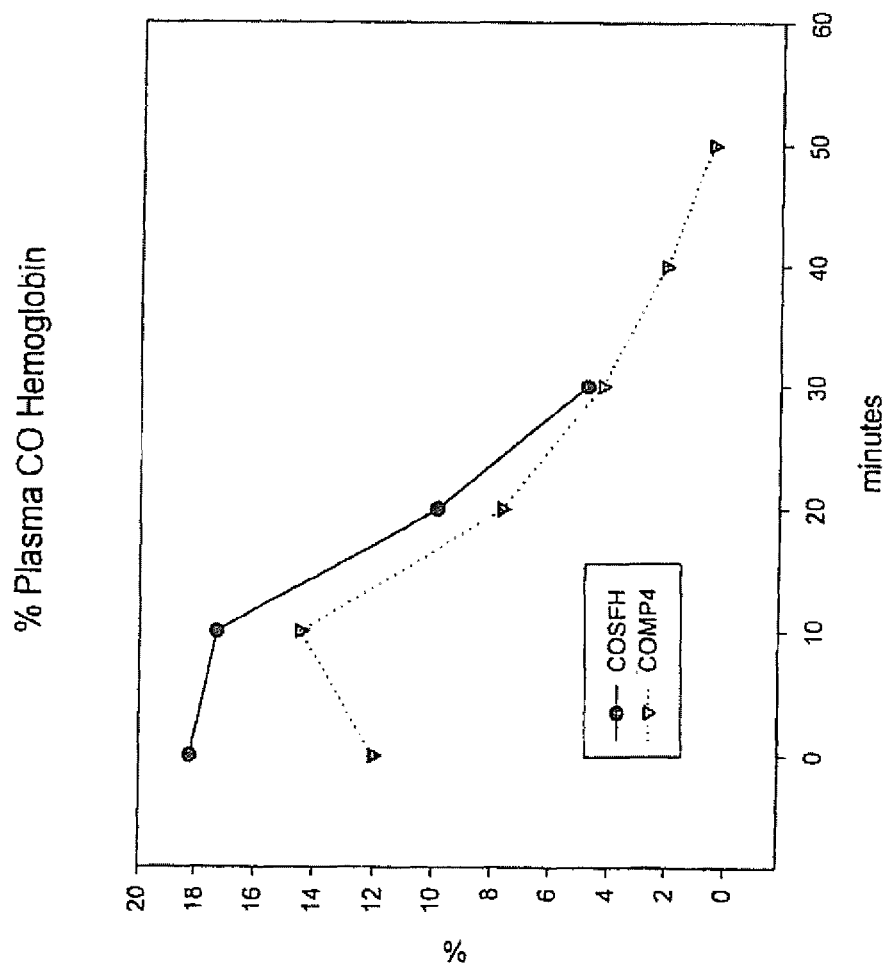
FIG. 17 depicts the changes in percent plasma CO hemoglobin after infusion of CO-SFH and COMP4.

The fall in hematocrit (FIG. 13) and total hemoglobin (FIG. 14) was similar in both groups of animals, indicating a similar degree of hemodilution. The initial plasma hemoglobin was slightly higher in the CO-SFH animals after exchange transfusion, but thereafter similar in all animals (FIG. 15). The total percent CO Hemoglobin was somewhat higher in COMP4 compared to CO-SFH (FIG. 16), but the percent saturation of plasma hemoglobin in the two groups was nearly the same (FIG. 17).

The conclusion from this experiment was that, first, CO-SFH is lethal. In spite of similar levels of total hemoglobin and percent COHb in the 2 experimental groups, the animals that received CO-SFH died very quickly and dramatically, while the animals that received COMP4 lived with little hemodynamic perturbabion throughout the observation period. The second conclusion from this experiment is that COMP4 functions as well in preventing shock as $O_2$-MP4.

The information presented above is provided to give those of ordinary skill in the art with a complete disclosure and description of how to make and use the preferred embodiments of the invention, and is not intended to limit the scope of what the inventor regards as his invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

Experiment 4

Stability Studies

Purpose

Test CO-MP4 stability at elevated temperature. CO-MP4 stability was tested by monitoring Met-Hb (Oxidized Hb) overtime by spectrophotometric method (CO-Ox 682).

Protocol

Oxy MP4 was converted into CO-MP4 by slowly purging carbon-monoxide (CO) through MP4 for 25 to 30 mins at room temperature.

COMP4 was stored under CO in glass bottles at 37° C. and 60° C.

Monitored total hemoglobin, met-Hb, CO-Hb and Oxy-Hb % by co-oximetry for up to 28 days and 8 hours respectively for samples stored at 37° C. and 60° C.

Results and Observations

TABLE 3

Stability at 37° C.

| Time (Days) | Met Hb % | CO Hb % | Oxy-Hb % |
|---|---|---|---|
| 1 | 3.2 | 95.3 | 0.2 |
| 2 | 2.1 | 96.4 | 0.0 |
| 3 | 1.5 | 97.2 | −0.2 |
| 3 | 1.7 | 96.8 | 0.0 |
| 4 | 1.5 | 97.2 | 0.0 |
| 7 | 1.7 | 96.8 | 0.0 |
| 9 | 1.5 | 97.2 | −0.1 |
| 11 | 1.8 | 96.9 | −0.3 |
| 15 | 1.5 | 97.1 | 0.0 |
| 22 | 1.4 | 97.2 | −0.2 |
| 28 | 1.5 | 97.1 | −0.3 |

TABLE 4

Stability at 60° C.

| Time (mins) | Met Hb % | CO Hb % | Oxy-Hb % |
|---|---|---|---|
| 0 | 2.3 | 97.0 | 0.2 |
| 30 | 2.0 | 95.1 | 2.3 |
| 90 | 1.7 | 94.8 | 3.1 |
| 120 | 1.7 | 94.6 | 3.4 |
| 180 | 1.5 | 94.7 | 3.4 |
| 240 | 1.4 | 94.8 | 3.4 |
| 300 | 1.2 | 94.7 | 3.7 |
| 360 | 1.0 | 95.1 | 3.4 |
| 420 | 1.1 | 94.9 | 3.8 |
| 480 | 0.9 | 95.2 | 3.4 |

Observations

COMP4 is very stable and did not get oxidized to met-Hb at 37° C. up to 28 days.

CO-MP4 did not oxidize at 60° C. in 8 hours.

CO-MP4 precipitated at higher temperatures (>75° C.).

MP4 is very stable when stored under 'CO'.

The invention claimed is:

1. A pharmaceutical composition for delivery of carbon monoxide comprising hemoglobin modified with a polyalkylene oxide polymer, and a pharmaceutically acceptable carrier, the hemoglobin modified with a polyalkylene oxide polymer comprising a maleimidyl moiety and polyalkylene oxide linked by a linker consisting of an alkylene or phenylene, the modified hemoglobin being complexed to carbon monoxide.

2. The composition of claim 1, wherein the carrier comprises an aqueous solution of salts, stabilizers, buffers, or a combination thereof.

3. The composition of claim 1, wherein the pharmaceutical composition further comprises the modified hemoglobin complexed to nitric oxide.

4. The composition of claim 1, wherein the hemoglobin does not contain free sulfhydryl groups.

5. The composition of claim 1 wherein the hemoglobin is from a fish, amphibian, insect, reptile, bird, nematode, annelid, human, cattle, swine, sheep, horse, or monkey.

6. The composition of claim 1, wherein the pharmaceutical composition is for subcutaneous, nasal, intramuscular, intraperitoneal or intravenous administration.

7. The composition of claim 6, wherein the pharmaceutical composition is for intravenous administration.

8. The composition of claim 1, wherein the pharmaceutical composition is an injectable, the concentration of the hemoglobin is 0.1-6 g/dL, and the carrier comprises an aqueous solution.

9. The composition of claim 1, wherein the linker is ethylene.

10. The composition of claim 1, wherein the surface-modified hemoglobin has the formula:

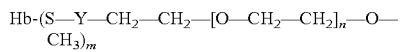

wherein:
- Hb is tetrameric hemoglobin;
- S is a thiol group of the hemoglobin;
- Y is succinimidylene;
- n is the number of oxyethylene units of the polyalkylene oxide polymer; and
- m is the number of maleimidyl-activated polyalkylene oxide polymers conjugated to the tetrameric hemoglobin.

11. The composition of claim 1, wherein the linker is phenylene.

12. The composition of claim 1, wherein the hemoglobin is human hemoglobin.

13. The composition of claim 1, wherein the hemoglobin is recombinant hemoglobin.

14. A method of treating a condition associated with vasoactivity or carbon monoxide metabolism, the method comprising administering to a human patient in need thereof the pharmaceutical composition of claim 1, wherein the condition associated with vasoactivity or carbon monoxide metabolism is hypertension, radiation damage, endotoxic shock, inflammation, autoimmune disease, vascular restenosis, sickle cell disease, apoptosis, xenotransplant rejection, Alzheimer's Disease, hypoxia, hyperoxia-induced injury, cancer, transplant rejection, post-operative ileus, arteriosclerosis, post-ischemic organ damage, myocardial infarction, angina, hemorrhagic shock, sepsis, penile erection dysfunction, adult respiratory distress syndrome, hepatic cirrhosis, cardiac hypertrophy, heart failure, ulcerative colitis or stroke.

15. The method of claim 14, wherein the condition is hemorrhagic shock.

16. The method of claim 14, wherein the condition is sickle cell disease.

17. The method of claim 14, wherein the condition is stroke.

18. The method of claim 14, wherein the condition is ulcerative colitis.

19. The method of claim 14 wherein the autoimmune disease is rheumatoid arthritis.

20. A method of promoting vasodilation, inhibiting platelet aggregation, stimulating neurotransmission or relaxing smooth muscle, the method comprising administering to a human patient in need thereof the pharmaceutical composition of claim 1.

* * * * *